(12) United States Patent
Begun

(10) Patent No.: US 6,485,498 B1
(45) Date of Patent: Nov. 26, 2002

(54) DEVICE WITH HAND GRIP FOR ABSORBING LIQUIDS, IN PARTICULAR FOR EAR CLEANING

(76) Inventor: Jacob Begun, Harneyaschim Street 7, 76804 Mazkeret Batya (IL)

( * ) Notice: Subject to any disclaimer, the term of this patent is extended or adjusted under 35 U.S.C. 154(b) by 0 days.

(21) Appl. No.: 09/600,815
(22) PCT Filed: Jan. 22, 1999
(86) PCT No.: PCT/IL99/00040
§ 371 (c)(1), (2), (4) Date: Sep. 26, 2000
(87) PCT Pub. No.: WO99/37262
PCT Pub. Date: Jul. 29, 1999

(30) Foreign Application Priority Data

Jan. 27, 1998 (IL) .................................. 123024

(51) Int. Cl.[7] ................................. A61F 11/00
(52) U.S. Cl. .......................................... 606/162; 604/1
(58) Field of Search ............................... 606/162, 109, 606/191, 199; 604/1, 2, 11, 904, 913

(56) References Cited

U.S. PATENT DOCUMENTS

| 92,980 | A | | 7/1869 | Lovell et al. |
|---|---|---|---|---|
| 102,351 | A | | 4/1870 | Wood et al. |
| 147,660 | A | | 2/1874 | Leiner |
| 2,510,490 | A | | 6/1950 | Ager |
| 2,842,790 | A | | 7/1958 | Castelli |
| 4,329,990 | A | | 5/1982 | Sneider |
| D269,811 | S | * | 7/1983 | Kaufman ............... D24/34 |
| 4,707,318 | A | * | 11/1987 | Can ..................... 264/138 |
| 4,804,362 | A | | 2/1989 | Enzo |
| 4,820,259 | A | | 4/1989 | Stevens |
| D318,531 | S | | 7/1991 | Nelson et al. |
| 5,147,288 | A | | 9/1992 | Schiavo |
| 2001/0001828 | A1 | * | 5/2001 | Begun .................... 606/162 |

FOREIGN PATENT DOCUMENTS

| GB | 2 153 230 | 8/1985 |
|---|---|---|
| JP | 86209695 | 11/1986 |
| WO | 98 01096 | 1/1998 |

* cited by examiner

Primary Examiner—John J. Calvert
Assistant Examiner—Shaun R Hurley
(74) Attorney, Agent, or Firm—Browdy and Neimark, P.L.L.C.

(57) ABSTRACT

A handheld applicator (1) for absorbing liquids for medical and personal hygiene purposes. The applicator (1) including at least one elongated support member (2) having a longitudinal axis (3) and an initially thin liquid absorbant pellet (6) securely fastened thereto at its distal end. The applicator (1) having a thin profile at least in the region of its distal end in an end view thereof in the direction of its associated longitudinal axis (3). The pellet (6) capable of absorbing liquid whereupon it expands significantly in at least one direction perpendicular to its associated longitudinal axis (3) in its associated end view to form a swab-like member (7).

4 Claims, 1 Drawing Sheet

DEVICE WITH HAND GRIP FOR ABSORBING LIQUIDS, IN PARTICULAR FOR EAR CLEANING

CROSS REFERENCE TO RELATED APPLICATION

The present application is the national stage under 35 U.S.C. 371 of PCT/IL99/00040, filed Jan. 22, 1999.

FIELD OF THE INVENTION

This invention relates to a handheld applicator for absorbing liquids for medical and personal hygiene purposes.

BACKGROUND OF THE INVENTION

Handheld applicators for absorbing liquids for medical and personal hygiene purposes, in particular ear cleaning, are illustrated and described inter alia in U.S. Pat. Nos. 92,980, 147,660, 102,351, 2,510,490, 2,842,790, 4,804,362, 5,147,288 and U.S. Des. 318,531. Such applicators generally include an elongated support member with a cotton or brush-like swab and suffer from the fact that they tend to push ear wax subsisting in an ear canal deeper thereinto on their insertion and thereby have a detrimental affect on a subject's hearing.

SUMMARY OF THE INVENTION

In accordance with the present invention, there is provided a handheld applicator for absorbing liquids for medical and personal hygiene purposes, the applicator comprising at least one elongated support member having a longitudinal axis and an initially thin liquid absorbent pellet securely fastened thereto at its distal end, the applicator having a substantially thin profile at least in the region of said distal end in an end view thereof in the direction of its associated longitudinal axis, said pellet capable of absorbing liquid whereupon it expands significantly in at least one direction perpendicular to its associated longitudinal axis in its associated end view to form a swab-like member.

The applicator of the present invention provides a convenient handheld device for a number of medical and personal hygiene purposes hitherto performed by conventional devices. In particular, the applicator of the present invention is suitable for absorbing water from a subjects ear canal whilst not pushing any earwax deeper thereinto on its initial insertion by virtue of its thin planar profile. Moreover, after its expansion, the swab-like member typically draws out subsisting earwax on its withdrawal from the ear. The pellet preferably contains alveolar cellulose known for its ability to absorb a volume of liquid considerably larger than its initial volume.

BRIEF DESCRIPTION OF THE DRAWINGS

In order to understand the invention and to see how it may be carried out in practice, a preferred embodiment will now be described, by way of a non-limiting example only, with reference to the accompanying drawings, in which.

DETAILED DESCRIPTION OF A PREFERRED EMBODIMENT

Figure 1:
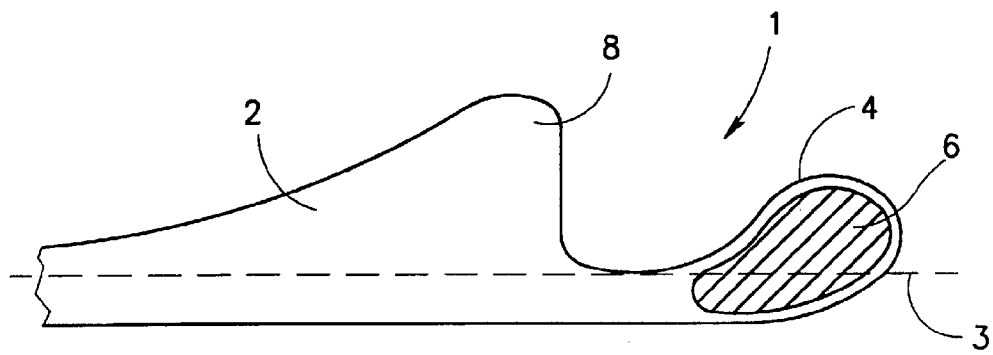
FIG. 1 is a top view of the applicator before use.
Figure 2:
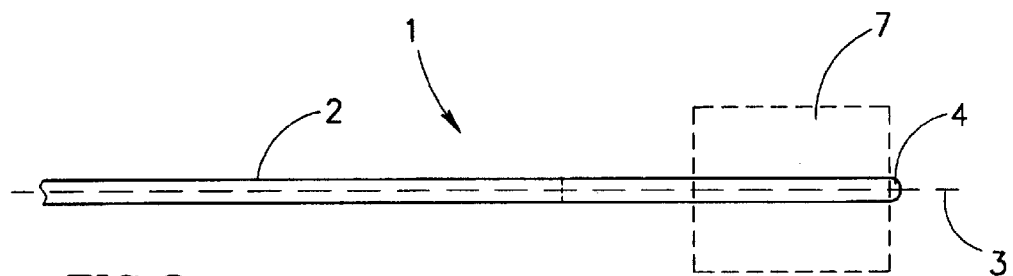
FIG. 2 is a side view of the applicator before use.
Figure 3:
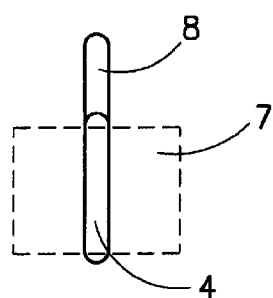
FIG. 3 is an end view of the applicator before use.
Figure 4:
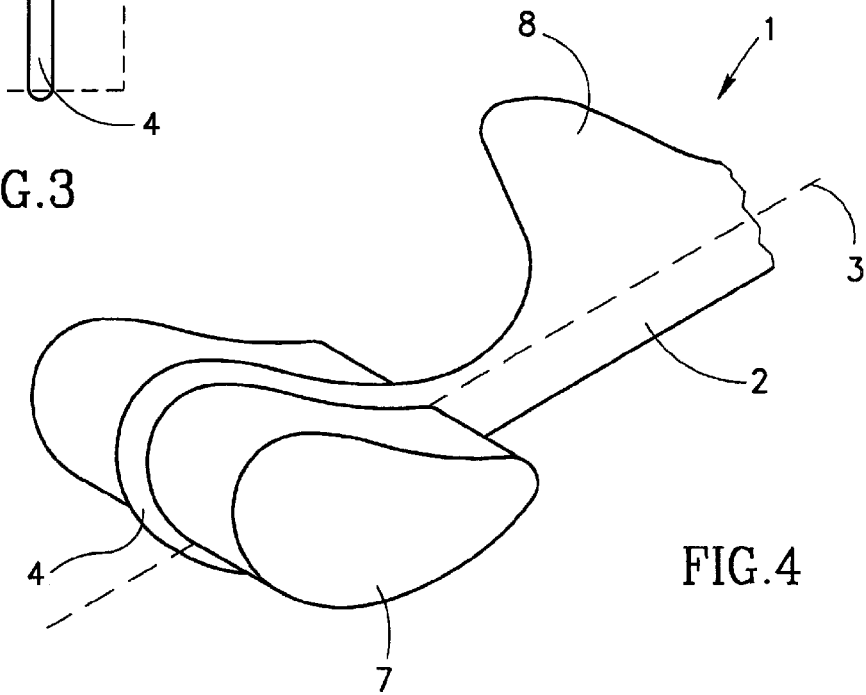
FIG. 4 is a perspective view of the applicator after use.

FIGS. 1–3 show a handheld applicator 1 including an elongated stem 2 (constituting a support member) with a longitudinal axis 3 and terminating in an oar-like shaped loop 4 for securely retaining a liquid absorbent pellet 6 of alveolar cellulose. The pellet 6 is initially of about the same thickness as the loop 4, namely 1 mm (see FIG. 3) and is designed to expand to a swab-like member 7 having a final thickness of about 10 mm on absorption of water (shown in dotted lines). The stem 2 has a stopper 8 for preventing the insertion of the loop 4 too deeply into a subject's ear.

In use, a subject grips the applicator 1 and inserts the loop 4 into his ear as far as the stopper 8 allows and gently rotates it and moves it in a to and fro action to contact water therein. Upon contacting water, the pellet 6 expands through absorption to form a swab-like member 7 securely retained in the loop 4 which encircles the midportion of its periphery. This allows continued manipulation of the swab-like member 7 which fills the cavity and absorbs water extant on its side walls. On removal from his ear, some of the excess earwax subsisting therein is removed.

While the present invention has been described with respect to a preferred embodiment, it will be appreciated that many variations, modifications and other applications of the invention can be made within the scope of the appended claims. For example, the support member may be bent or twisted relative to its longitudinal axis. Also, the loop may not completely encircle the pellet, which may only partially fill the loop. An applicator may have more than one pellet, which may be formed from polyactylate, or any other absorbing material.

What is claimed is:

1. A handeld applicator (1) for absorbing liquids for medical and personal hygiene purposes and in particular for cleaning the ear canal, the applicator comprising at least one elongated support member (2) having a longitudinal axis (3) and an initially thin liquid absorbent pellet (6) securely fastened thereto at its distal end, the applicator having a substantially thin profile at least in the region of said distal end in an end view thereof in the direction of its associated longitudinal axis, said pellet capable of absorbing liquid whereupon it expands significantly in at least one direction perpendicular to its associated longitudinal axis in its associated end view to form a swab-like member (7) characterized in that said pellet has a height substantially greater than its width in said end view and which expands on absorption of liquid significantly in said widthwise direction only.

2. The applicator according to claim 1 wherein said support member terminates in an aperture for receiving said pellet.

3. The applicator according to claim 2 wherein said support member terminates in an oar-like shaped loop (4).

4. The applicator according to claim 1 wherein said pellet contains alveolar cellulose.

* * * * *